(12) United States Patent
Wu et al.

(10) Patent No.: US 12,201,689 B1
(45) Date of Patent: Jan. 21, 2025

(54) CHIMERIC ANTIGEN RECEPTOR T CELL AND CONSTRUCTION METHOD THEREOF, AND ANTITUMOR DRUG

(71) Applicant: Guangzhou Morui Pharmaceutical Technology Co., Ltd., Guangdong (CN)

(72) Inventors: Dousheng Wu, Guangdong (CN); Yang Yang, Guangdong (CN)

(73) Assignee: Guangzhou Morui Pharmaceutical Technology Co., Ltd., Guangzhou (CN)

(*) Notice: Subject to any disclaimer, the term of this patent is extended or adjusted under 35 U.S.C. 154(b) by 0 days.

(21) Appl. No.: 18/426,287

(22) Filed: Jan. 29, 2024

(30) Foreign Application Priority Data

Jul. 20, 2023 (CN) .......................... 202310891875.4

(51) Int. Cl.
| | | |
|---|---|---|
| *A61K 48/00* | (2006.01) | |
| *A61K 35/17* | (2015.01) | |
| *A61K 39/00* | (2006.01) | |
| *A61P 35/00* | (2006.01) | |
| *C07H 21/04* | (2006.01) | |
| *C07K 16/30* | (2006.01) | |
| *C12N 5/0783* | (2010.01) | |
| *C12N 15/63* | (2006.01) | |
| *C12N 15/86* | (2006.01) | |
| *A01K 67/00* | (2006.01) | |

(52) U.S. Cl.
CPC .......... *A61K 39/4631* (2023.05); *A61K 35/17* (2013.01); *A61P 35/00* (2018.01); *C07K 16/3023* (2013.01); *C12N 5/0636* (2013.01); *C12N 15/86* (2013.01); *A61K 2239/13* (2023.05); *A61K 2239/21* (2023.05); *A61K 2239/22* (2023.05); *A61K 2239/55* (2023.05); *C07K 2317/24* (2013.01); *C12N 2510/00* (2013.01); *C12N 2740/15043* (2013.01)

(58) Field of Classification Search
CPC ..... A61K 39/4631; A61K 35/17; A61P 35/00; C12N 15/86; C12N 2510/00
See application file for complete search history.

(56) References Cited

U.S. PATENT DOCUMENTS

| | | | |
|---|---|---|---|
| 9,597,357 B2 * | 3/2017 | Gregory | A61K 39/464409 |
| 11,673,953 B2 * | 6/2023 | Zhang | C07K 16/28 |
| | | | 424/133.1 |

FOREIGN PATENT DOCUMENTS

WO WO2020/213710 * 10/2020

OTHER PUBLICATIONS

Moon et al. Aquaporins in cancer biology. Front. Oncol. 12:782829. doi: 10.3389/fonc.2022.782829, 25 pages, (Year: 2022).*

* cited by examiner

*Primary Examiner* — Quang Nguyen

(57) ABSTRACT

Disclosed are a chimeric antigen receptor T (CAR-T) cell and a construction method thereof, and an antitumor drug. In the present application, aquaporin 3 (AQP3) is adopted as a novel anti-cancer target, and AQP3 is highly expressed in both tumor cells and tumor stromal cells and can mediate the transport of both water and glycerol, which is conducive to breakage of a physical barrier of a tumor and promotes CAR-T cells to well infiltrate into a tumor to kill the tumor. The chimeric antigen receptor (CAR) fusion protein of the present application can be used in the treatment of AQP3-positive malignant tumors, and especially, when used in the treatment of non-small cell lung cancer (NSCLC), the CAR fusion protein exhibits a significant therapeutic effect. In addition, when used in the treatment of lung cancer, the CAR fusion protein causes little damage to a normal tissue and exhibits high safety.

2 Claims, 9 Drawing Sheets

Specification includes a Sequence Listing.

US 12,201,689 B1

CHIMERIC ANTIGEN RECEPTOR T CELL AND CONSTRUCTION METHOD THEREOF, AND ANTITUMOR DRUG

CROSS-REFERENCE TO RELATED APPLICATION

The present application claims priority from Chinese Patent Application No. 202310891875.4 filed on Jul. 20, 2023, the contents of which are incorporated herein by reference in their entirety.

TECHNICAL FIELD

The present application relates to the technical field of cell biology, and in particular to a chimeric antigen receptor T (CAR-T) cell and a construction method thereof, and an anti-tumor drug.

REFERENCE TO SEQUENCE LISTING

The Sequence Listing XML file submitted via the USPTO Patent Center, with a file name of "Sequence Listing_SCH-23240-USPT.xml", a creation date of Dec. 25, 2023, and a size of 7 KB, is part of the specification and is incorporated in its entirety by reference herein.

BACKGROUND

With the emergence of tumor immunotherapy, the technology of using engineered CAR-T cells to specifically target tumor cells for tumor killing has made great progress. The CAR-T therapy has achieved remarkable results in the treatment of hematological malignancies. Some breakthroughs have also been made by the CAR-T therapy in the treatment of solid tumors, but the therapeutic effect and use of CAR-T therapy for solid tumors have been greatly limited due to various inhibitory factors of solid tumors and side effects of CAR-T itself such as cytokine storms. The lack of specific tumor antigens has become an important factor limiting the further development of CAR-T therapy. Therefore, it is important to overcome the complicated microenvironment of solid tumor and find specific tumor antigen for CAR-T therapy.

According to statistical data of the World Health Organization (WHO), there are about 19.3 million new cancer cases and 9.9 million cancer deaths worldwide. Lung cancer is the second most common cancer and is also a leading cause for cancer deaths. In 2020, there were about 2.2 million new lung cancer cases and 1.8 million lung cancer deaths, where non-small cell lung cancer (NSCLC) cases account for about 80% of all lung cancer cases. At present, the treatment of lung cancer is still based on conventional surgery, with radiotherapy and chemotherapy as adjuvant means. Immunotherapy and targeted therapy emerging in recent years have also brought dawn to the cure of lung cancer. Although various new drugs and new treatment for lung cancer are emerging, there are still few effective therapies to cure the disease. The extensive research on CAR-T tumor therapy is expected to bring a new hope for the treatment of lung cancer. In the current CAR-T therapy for lung cancer, the target ability of CAR-T cells is reduced due to the lack of a significantly specific antigen for lung cancer in most cases, and due to a complicated environment of solid tumor, most CAR-T cells are difficult to enter the tumor to play a role. Therefore, it is of vital importance for the treatment of lung cancer to find a specific antigen of lung cancer for modifying T cells and increase the tumor infiltration and activity of CAR-T cells.

With the vigorous development of research on CAR-T immunotherapy for tumors, the CAR-T cell therapy has been updated to the fifth generation. During construction of CAR-T cells, it is necessary to comprehensively consider a complexity degree of T cell modification and a function of CAR-T in a practical application. According to clinical trials, the second-generation CAR-T and third-generation CAR-T have relatively stable and efficient effects. With respect to the CAR-T therapy for lung cancer, a large number of preclinical and clinical trials have been approved for implementation. However, due to a variety of inhibitory factors in solid tumors, a therapeutic effect of CAR-T is far from reaching an expected level. For example, due to an immunosuppressive microenvironment of solid tumor, after T cells enter the tumor microenvironment, a killing ability of the T cells is inhibited and the T cells cannot continuously play a role; during the occurrence and development of a tumor, an antigen escape phenomenon weakens a targeting ability of CAR-T and reduces a tumor-killing effect; and the presence of cancer-associated fibroblasts (CAFs) also greatly limits the infiltration of CAR-T cells into the solid tumor. Although preclinical studies and clinical trials of CAR-T in the treatment of NSCLC emerge one after another, a therapeutic effect of CAR-T cells for solid tumor is still very limited, and there is a lack of an effective and specific target to overcome a special physical barrier including both the extracellular matrix (ECM) and CAFs in a lung cancer tissue. Therefore, the breakage of an immunosuppressive microenvironment of solid tumor and the discovery of a specific tumor antigen as a tumor target of the CAR-T therapy are scientific problems that need to be solved urgently.

Aquaporin 3 (AQP3) has an effect of reabsorbing water and glycerol, and is distributed in basolateral cell membranes of collecting ducts of renal medulla. AQP3 can promote the migration of cells by transporting water and glycerol to form pseudopodia, and cause the proliferation of cells by maintaining a high glycerol level in the cells to produce ATP and lipids. Various studies have shown that the up-regulation of an expression level of AQP3 can promote tumorigenesis. It has been reported that AQP3 is highly expressed in lung adenocarcinoma, is closely related to prognosis, and can regulate the autophagy of lung cancer cells by mediating the transmembrane transport of reactive oxygen species (ROS), thereby affecting the progression of lung cancer. In addition, AQP3 is highly expressed in breast cancer, kidney cancer, gastrointestinal tumors, or the like. Therefore, this target is expected to address a wide range of tumor types. There are currently no studies on the use of AQP3 as a novel tumor target for tumor immunotherapy.

SUMMARY

An objective of the present application is to overcome the shortcomings of the prior art and provide a CAR-T cell and a construction method thereof, and an anti-tumor drug. In the present application, an anti-AQP3 antibody with high affinity is found as an extracellular recognition region of CAR-T to construct a second-generation CAR-T system for the treatment of lung cancer. AQP3 is highly expressed on a surface of lung cancer cells and in stromal cells and can regulate the transport of water and glycerol in cells. Thus, when AQP3 is adopted as a target, tumor cells can be killed while disintegrating a tumor barrier, which increases the efficacy of CAR-T cells.

To achieve the objective above, the present application adopts the following technical solutions:

In a first aspect, the present application provides a chimeric antigen receptor (CAR) fusion protein, including from N-terminus to C-terminus:
(i) an extracellular recognition region including a single-chain variable fragment (ScFv), where the ScFv targets an AQP3 antigen, and the ScFv has an amino acid sequence encoded by a polynucleotide shown in SEQ ID NO: 1;
(ii) a hinge region;
(iii) a transmembrane region; and
(iv) an intracellular stimulatory signaling domain.

In the present application, AQP3 is innovatively adopted as a novel anti-cancer target, and AQP3 is highly expressed in both tumor cells and tumor stromal cells and can mediate the transport of both water and glycerol, which is conducive to breakage of a physical barrier of a tumor to kill the tumor. The CAR fusion protein prepared by the present application can be used in the treatment of AQP3-positive malignant tumors, and especially, when used in the treatment of NSCLC, the CAR fusion protein exhibits a significant therapeutic effect. In addition, when used in the treatment of lung cancer, the CAR fusion protein causes little damage to a normal tissue and exhibits high safety.

As a preferred embodiment of the CAR fusion protein of the present application, the hinge region is a CD8α hinge region; the transmembrane region is a CD8α transmembrane region, and the intracellular stimulatory signaling domain is 4-1BB-CD3ξ.

As a preferred embodiment of the CAR fusion protein of the present application, the extracellular recognition region has an amino acid sequence shown in SEQ ID NO: 3.

As a preferred embodiment of the CAR fusion protein of the present application, the CAR fusion protein has an amino acid sequence encoded by a polynucleotide shown in SEQ ID NO: 2.

As a preferred embodiment of the CAR fusion protein of the present application, the CAR fusion protein has an amino acid sequence shown in SEQ ID NO: 4.

In a second aspect, the present application provides a nucleic acid encoding the CAR fusion protein described above.

In a third aspect, the present application provides a vector, including the nucleic acid described above.

As a preferred embodiment of the vector of the present application, the vector is selected from the group consisting of DNA, RNA, a plasmid, a lentiviral vector, and a combination thereof, and preferably, the vector is a lentiviral vector. The vector may also be a vector commonly used in the prior art, as long as the technical effect of the present application can be allowed.

As a preferred embodiment of the vector of the present application, a nucleotide sequence shown in SEQ ID NO: 2 is ligated to a lentiviral vector through homologous recombination.

In a fourth aspect, the present application provides a CAR-T cell expressing the CAR fusion protein described above (namely, an AQP3-CAR-T cell).

A CAR molecule in the CAR-T cell includes an extracellular recognition region, a hinge region, a transmembrane region, and an intracellular stimulatory signaling domain that are sequentially ligated in series, where the extracellular recognition region is a protein binding site of AQP3 and the intracellular stimulatory signaling domain is 4-1BB. The constructed CAR-T cell can significantly kill lung cancer cells in vivo and in vitro, and can treat AQP3-positive malignant tumors and can exhibit a significant therapeutic effect especially in the treatment of NSCLC. In addition, when used in the treatment of lung cancer, the CAR-T cell causes little damage to a normal tissue and exhibits high safety, which is worthy of further research and promotion.

The extracellular recognition region of the CAR-T cell therapy in the present application is based on the use of an NSCLC-specific antigen AQP3 as a tumor immunotherapy target, and an anti-AQP3 antibody with high affinity is adopted as the extracellular recognition region. AQP3 is not only expressed on tumor cells of lung cancer tissue, but also expressed on non-tumor cells such as tumor stromal cells, and can mediate the transport of water and glycerol, which can promote the well infiltration of CAR-T cells into a tumor. The target has a more effective theoretical basis than the current targets of CAR-T therapy for lung cancer.

In a fifth aspect, the present application provides a construction method of a CAR-T cell expressing the CAR fusion protein described above, including the following step: transforming the nucleic acid or the vector into a T cell to obtain the CAR-T cell, where the extracellular recognition region of the CAR-T cell is a protein binding site of AQP3.

Preferably, the construction method of the CAR-T cell provided in the present application includes the following specific steps:

I. Construction of the CAR fusion protein: sequentially ligating the signal peptide of CD8a, the extracellular recognition region (including an ScFv, where the ScFv targets an AQP3 antigen, and the ScFv has an amino acid sequence encoded by a polynucleotide shown in SEQ ID NO: 1), the CD8α extracellular region, and the CD8α transmembrane region to obtain the CAR fusion protein, where the CAR fusion protein has an amino acid sequence encoded by a polynucleotide shown in SEQ ID NO: 2 and an amino acid sequence of the CAR fusion protein is shown in SEQ ID NO: 4.

II. Construction of a lentiviral vector and packaging the lentivirus: ligating the nucleotide sequence of the CAR fusion protein to a lentiviral vector through homologous recombination, and determining the accuracy of an overexpression fragment through next-generation sequencing (NGS); extracting plasmids and purifying the plasmids, transfecting the plasmids and lentiviral packaging plasmids into 293 FT cells according to a specified ratio, and cultivating the cells for 72 hours; and collecting resulting supernatant and concentrating the supernatant to obtain a viral solution, determining a titer of the viral solution, and storing the viral solution in an ultra-low temperature freezer at −80° C.

III. Isolation of T cells and expansion cultivation of the T cells: collecting peripheral venous blood from a healthy adult, isolating peripheral blood mononuclear cells (PBMCs) from the peripheral venous blood by a ficoll separation method, isolating T cells by CD3-positive magnetic beads, and subjecting the T cells to expansion cultivation; and transfecting resulting T cells with lentivirus prepared in Step II, and subjecting transfected T cells to expansion cultivation to obtain the AQP3-CAR-T cell.

In a sixth aspect, the present application provides a drug or preparation for preventing and/or treating a tumor, including the CAR fusion protein, the nucleic acid, the vector, or the CAR-T cell.

The CAR fusion protein and the CAR-T cell prepared by the present application can be used in the treatment of AQP3-positive malignant tumors, and exhibits a significant therapeutic effect especially in the treatment of NSCLC. In in vivo and in vitro experiments, the CAR-T cell (namely, an AQP3-CAR-T cell) prepared in the present application can significantly kill lung cancer cells, which provides a novel target for the treatment of NSCLC. In addition, when used in the treatment of lung cancer, the AQP3-CAR-T causes little damage to a normal tissue and exhibits high safety, which is worthy of further research and promotion.

As a preferred embodiment of the drug or preparation in the present application, the tumor is an AQP3-positive malignant tumor.

As a preferred embodiment of the drug or preparation in the present application, the AQP3-positive malignant tumor is NSCLC.

As a preferred embodiment of the drug or preparation in the present application, the AQP3-positive malignant tumor includes NSCLC lines H460 and A549.

In an in vitro experiment, the CAR-T cell constructed in the present application also exhibits an effective therapeutic effect. When used in the treatment of a lung cancer cell line H460 with high expression of AQP3, the CAR-T cell exhibits a strong effect of killing tumor cells in the absence of an obvious effect of normal T cells. After the CAR-T cell is co-incubated with tumor cells for a specified period, the secretion of IFN-γ is proportional to a killing ability of the CAR-T cell, and the secretion of IFN-γ in the group of killing H460 cells via the AQP3-CAR-T cells is significantly higher than that in other groups, with significant differences. In addition, in an in vivo experiment, the AQP3-CAR-T cell can significantly suppress a subcutaneously transplanted tumor growth by lung cancer cell line H460. Pathological sections show that there is obvious large-area cell necrosis in the tumor tissue in the group of the CAR-T cell therapy.

The present application also provides a preparation including the CAR fusion protein described in the first aspect, the nucleic acid described in the second aspect, the vector described in the third aspect, or the CAR-T cell described in the fourth aspect, and a pharmaceutically acceptable carrier, diluent, or excipient.

In another preferred embodiment, the preparation is a liquid preparation.

In another preferred embodiment, a dosage form of the preparation is an injection.

In another preferred embodiment, a concentration of the CAR-T cell in the preparation is $1\times10^3$ cells/mL to $1\times10^8$ cells/mL and preferably $1\times10^7$ cells/mL.

Compared with the prior art, the present application has the following beneficial effects:

In the present application, AQP3 is innovatively adopted as a novel anti-cancer target, and AQP3 is highly expressed in both tumor cells and tumor stromal cells and can mediate the transport of both water and glycerol, which is conducive to breakage of a physical barrier of a tumor and promotes CAR-T cells to well infiltrate into a tumor to kill the tumor. The CAR fusion protein prepared by the present application can be used in the treatment of AQP3-positive malignant tumors, and especially, when used in the treatment of NSCLC, the CAR fusion protein exhibits a significant therapeutic effect. In addition, when used in the treatment of lung cancer, the CAR fusion protein causes little damage to a normal tissue and exhibits high safety.

In lung cancer, AQP3 is highly expressed on a surface of tumor cells. The selection of AQP3 as a target for CAR-T therapy makes up for the lack of an effective specific target for CAR-T therapy of NSCLC and the difficulty of CAR-T to overcome a barrier of tumor stromal cells, and can also inhibit the promotion of AQP3 on the progression of a tumor, which is a therapeutic direction with many advantages.

The AQP3-CAR-T cell of the present application also provides a direction for the treatment of other AQP3-positive tumor types, and beneficial results of in vivo and in vitro experiments of the AQP3-CAR-T cell have been obtained in treatment of lung tumors with high AQP3 expression. The therapeutic mechanism of AQP3-CAR that relies on the expression of AQP3 to play a role has extensive application values. The present application makes up for the shortcoming that there is a single target for lung cancer treatment, and provides a novel target and idea for lung cancer treatment, which is worthy of further research and promotion.

DETAILED DESCRIPTION

Figure 1:
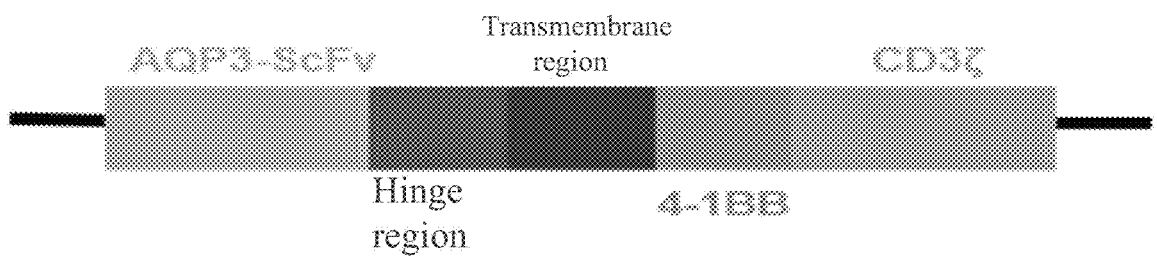
FIG. 1 is a schematic diagram of the construction of AQP3-CAR.

To well explain the objective, technical solutions, and advantages of the present application, the present application will be further explained below with reference to the accompanying drawings and specific embodiments.

In order to make the objective, technical solutions, and advantages of the embodiments of the present application clear, the technical solutions in the embodiments of the present application are described clearly and completely below. Apparently, the described embodiments are some rather than all of the embodiments of the present application. All other embodiments obtained by those of ordinary skill in the art based on the embodiments of the present application without creative efforts should fall within the protection scope of the present application.

In the present application, the technical features described openly include a closed technical solution composed of the listed features, and also include an open technical solution including the listed features.

In the present application, unless otherwise specified, a numerical interval involved is considered as continuous, and includes minimum and maximum values of the range and any value between the minimum and maximum values. Further, when the range refers to an integer, any integer between the minimum and maximum values of the range is included. In addition, when a plurality of ranges are provided to describe a feature or characteristic, the ranges can be combined. In other words, unless otherwise indicated, all ranges disclosed herein shall be understood to include any and all sub-ranges belonging in the ranges.

The present application has no special limitations on the specific dispersion and stirring methods.

All of the reagents or instruments used in the present application that are not specified with manufacturers are conventional commercially-available products.

In addition, the terms such as "first" and "second" are used only for the purpose of description and should not be construed as indicating or implying a relative importance, or implicitly indicating a quantity of indicated technical features. Therefore, features defined by "first" and "second" may explicitly or implicitly include at least one of the features. In the description of the present application, "a plurality of" means at least two, such as two or three, unless otherwise clearly and specifically limited.

In the following embodiments, unless otherwise specified, the experimental methods used are conventional, and the materials and reagents used are commercially available.

As used herein, "CAR" refers to a fusion protein that includes an extracellular domain capable of binding to an antigen, a transmembrane domain derived from a different polypeptide from the extracellular domain, and at least one intracellular domain. "CAR" is also known as "chimeric receptor", "T-body", or "chimeric immune receptor (CIR)". The "extracellular domain capable of binding to an antigen" refers to any oligopeptide or polypeptide capable of binding to a specified antigen. The "intracellular domain" refers to any known oligopeptide or polypeptide that transmits a signal to activate or inhibit a biological process in cells.

As used herein, the "domain" refers to a region in a polypeptide that is independent of other regions and can be folded into a specific structure.

As used herein, the "tumor antigen" refers to a biomolecule with antigenicity whose expression causes cancer.

As used herein, the "ScFv" refers to a single-chain polypeptide derived from an antibody that retains an ability of binding to an antigen. Examples of the ScFv include antibody polypeptides produced by recombinant DNA technology, where Fv regions of heavy chain (H chain) and light chain (L chain) fragments of an immunoglobulin are linked by a spacer sequence. Various methods for preparing the ScFv are well known to those skilled in the art.

A linker can be introduced between an extracellular recognition region and a transmembrane region of CAR. As used herein, the term "linker" generally refers to any oligopeptide or polypeptide that links a transmembrane region to an extracellular recognition region of a polypeptide chain. The linker may include 0 to 300 amino acids, preferably 2 to 100 amino acids, and more preferably 3 to 50 amino acids.

In a preferred embodiment of the present application, the extracellular domain of the CAR provided by the present application includes an antigen-binding domain targeting AQP3. When expressed in T cells, the CAR of the present application allows antigen recognition based on antigen binding specificity.

The CAR of the present application includes a guide sequence, an extracellular recognition region, a hinge region, a transmembrane region, and an intracellular stimulatory signaling domain that are sequentially ligated in series. The extracellular recognition region includes a target-specific binding element (also known as an antigen-binding domain). The antigen-binding domain is usually an ScFv. A size of the ScFv is generally ⅙ of a size of a complete antibody. A single-chain antibody is preferably an amino acid sequence encoded by a nucleotide chain. As a preferred implementation of the present application, the ScFv includes an antibody specifically recognizing an AQP3 antigen highly expressed in a tumor, and is preferably a single-chain antibody. In the present application, the ScFv targets an AQP3 tumor antigen, and the ScFv has an amino acid sequence encoded by a polynucleotide shown in SEQ ID NO: 1.

For the hinge region and transmembrane region (transmembrane domain), the CAR can be designed to include a transmembrane domain fused to the extracellular domain of the CAR. In an embodiment, a transmembrane domain naturally associated with one of the domains in the CAR is used. In some cases, a transmembrane domain may be selected or modified through amino acid substitutions to prevent such a domain from binding to a transmembrane domain of a same or different surface membrane protein, thereby minimizing an interaction with other members of the receptor complex.

The present application provides a CAR fusion protein, including from N-terminus to C-terminus: (i) an extracellular recognition region including an ScFv, where the ScFv targets an AQP3 tumor antigen, and the ScFv has an amino acid sequence encoded by a polynucleotide shown in SEQ ID NO: 1; (ii) a hinge region; (iii) a transmembrane region; and (iv) an intracellular stimulatory signaling domain. The CAR fusion protein further includes a guide sequence, where the guide sequence is a signal peptide of CD8a, the hinge region is a CD8α hinge region, the transmembrane region is a CD8α transmembrane region, and the intracellular stimulatory signaling domain is 4-1BB-CD3ς. In the CAR fusion protein of the present application, a high-affinity site of the AQP3 antibody is adopted as an extracellular recognition region, a partial extracellular region and a complete transmembrane region of CD8α are linked to form a linkage structure, intracellular regions of 4-1BB and CD3ς are linked sequentially, and 5 linker amino acid fragments are used as a linker at different linkage sites, as shown in FIG. 1.

The present application also provides a CAR-T cell targeting the AQP3 tumor antigen. The CAR-T cell can significantly kill lung cancer cells in vivo and in vitro, and can treat AQP3-positive malignant tumors, and especially when used in the treatment of NSCLC, the CAR-T cell can exhibit a significant therapeutic effect. In addition, when used in the treatment of lung cancer, the CAR-T cell causes little damage to a normal tissue and exhibits high safety, which is worthy of further research and promotion.

The nucleotide sequences and amino acid sequences involved in the present application are as follows:

SEQ ID NO: 1:
GAGGTGAAGCTGGTGGAGAGCGGCGGCGACCTGGTGAAGCCCGGCGGCA
GCCTGAAGATCAGCTGCGCCGCCAGCGGCTTCACCTTCAGCAGCTACGG
CATGAGCTGGGTGAGGCAGACCCCCGACAAGAGGCTGGAGTGGGTGGCC
ACCATCAGCAGGAGGAGCACCTACACCTACTACCCCGACAGCGTGCAGG
GCAGGTTCACCATCAGCAGGGACAACGCCAAGAACACCCTGTACCTGCA
GATGAGCAGCCTGAAGAGCGAGGACACCGCCATGTACTACTGCGCCAGG
CTGAGCCTGTACGACTACGACGGCGCCAGGTACACCATGGACTACTGGG
GCCAGGGCACCAGCGTGACCGTGAGCAGCGACATCAAGATGACCCAGAG
CCCCAAGTTCATGAGCACCAGCGTGGGCGACAGGGTGAGCATCACCTGC
AAGGCCAGCCAGGACGTGGGCACCGCCGTGGCCTGGTACCAGCAGAAGC
CCGGCCAGAGCCCCAAGCTGCTGATCTACTGGGCCAGCACCAGGCACAC
CGGCGTGCCCGACAGGTTCACCGGCAGCGGCAGCGGCACCGACTTCACC
CTGACCATCAGCAACGTGCAGAGCGAGGACCTGGCCGACTACTTCTGCC
AGCAGTACAGCAGCTACCACACCTTCGGCGCCGGCACCAAGCTGGAGAT
CAAG

SEQ ID NO: 2:
gctggctaggtaagcttgatgctagccaccatggccttaccagtgaccg
ccttgctcctgccgctggccttgctgctccacgccgccaggccgGAGGT
GAAGCTGGTGGAGAGCGGCGGCGACCTGGTGAAGCCCGGCGGCAGCCTG
AAGATCAGCTGCGCCGCCAGCGGCTTCACCTTCAGCAGCTACGGCATGA
GCTGGGTGAGGCAGACCCCCGACAAGAGGCTGGAGTGGGTGGCCACCAT
CAGCAGGAGGAGCACCTACACCTACTACCCCGACAGCGTGCAGGGCAGG
TTCACCATCAGCAGGGACAACGCCAAGAACACCCTGTACCTGCAGATGA
GCAGCCTGAAGAGCGAGGACACCGCCATGTACTACTGCGCCAGGCTGAG
CCTGTACGACTACGACGGCGCCAGGTACACCATGGACTACTGGGGCCAG
GGCACCAGCGTGACCGTGAGCAGCggtggtggtggttctggcggcggcg
gctccggtggtggtggttctggcggcggcggctccGACATCAAGATGAC
CCAGAGCCCCAAGTTCATGAGCACCAGCGTGGGCGACAGGGTGAGCATC
ACCTGCAAGGCCAGCCAGGACGTGGGCACCGCCGTGGCCTGGTACCAGC
AGAAGCCCGGCCAGAGCCCCAAGCTGCTGATCTACTGGGCCAGCACCAG
GCACACCGGCGTGCCCGACAGGTTCACCGGCAGCGGCAGCGGCACCGAC
TTCACCCTGACCATCAGCAACGTGCAGAGCGAGGACCTGGCCGACTACT
TCTGCCAGCAGTACAGCAGCTACCACACCTTCGGCGCCGGCACCAAGCT
GGAGATCAAGaccacgacgccagcgccgcgaccaccaacaccggcgccc
accatcgcgtcgcagccctgtccctgcgcccagaggcgtgccggccag
cggcggggggcgcagtgcacacgaggggggctggacttcgcctgtgatat
ctacatctgggcgcccttgg SEQ ID NO: 3:
EVKLVESGGDLVKPGGSLKISCAASGFTFSSYGMSWVRQTPDKRLEWVA
TISRRSTYTYYPDSVQGRFTISRDNAKNTLYLQMSSLKSEDTAMYYCAR
LSLYDYDGARYTMDYWGQGTSVTVSSDIKMTQSPKFMSTSVGDRVSITC
KASQDVGTAVAWYQQKPGQSPKLLIYWASTRHTGVPDRFTGSGSGTDFT
LTISNVQSEDLADYFCQQYSSYHTFGAGTKLEIK SEQ ID NO: 4:
AGVSLMLATMALPVTALLLPLALLLHAARPEVKLVESGGDLVKPGGSLK
ISCAASGFTFSSYGMSWVRQTPDKRLEWVATISRRSTYTYYPDSVQGRF
TISRDNAKNTLYLQMSSLKSEDTAMYYCARLSLYDYDGARYTMDYWGQG
TSVTVSSGGGGSGGGGSGGGGSGGGGSDIKMTQSPKFMSTSVGDRVSIT
CKASQDVGTAVAWYQQKPGQSPKLLIYWASTRHTGVPDRFTGSGSGTDF
TLTISNVQSEDLADYFCQQYSSYHTFGAGTKLEIKTTTPAPRPPTPAPT
IASQPLSLRPEACRPAAGGAVHTRGLDFACDIYIWAPL.

Example 1 An AQP3-CAR-T Cell and a Construction Method Thereof

In this example, a construction method of an AQP3-CAR-T cell was provided, including the following steps:
I. Determination of an overexpression sequence of a second-generation CAR: 50 amino acids in an extracellular region of CD8α (an amino acid sequence of the extracellular recognition region is shown in SEQ ID NO: 3, and a nucleotide sequence of the ScFv in the extracellular recognition region is shown in SEQ ID NO: 1), a transmembrane region of CD8a, and an intracellular co-stimulatory signaling domain of 4-1BB and CD3 were sequentially linked by a signal peptide of CD8a. The basic design idea was in line with the second-generation CAR-T, but there was a sequence of 5 amino acids other than the intracellular region as a linker between any two independent molecules to constitute the CAR fusion protein. A nucleotide sequence of the CAR fusion protein was shown in SEQ ID NO: 2; and an amino acid sequence of the CAR fusion protein was shown in SEQ ID NO: 4. The synthesized CAR fusion protein would be used for construction of a lentiviral plasmid.

Figure 2:
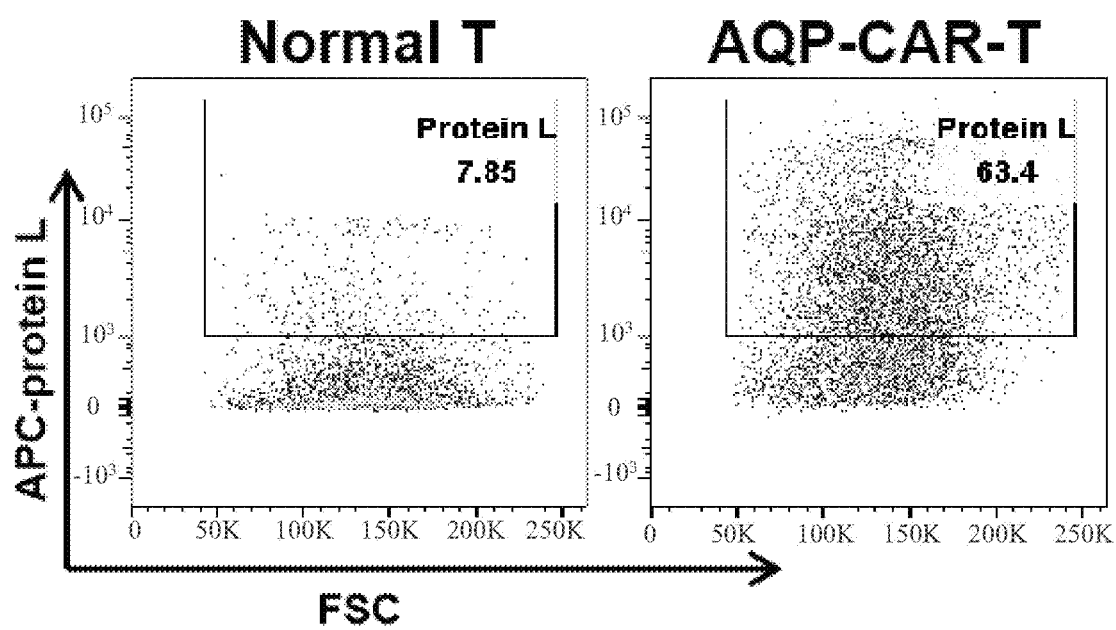
FIG. 2 shows the efficiency of transfection of AQP3-CAR into T cells.

II. Construction of a lentiviral vector and packaging of a lentivirus: A DNA sequence of the synthesized CAR fusion protein (AQP3-CAR) was ligated to an overexpression lentiviral plasmid (pLenti-EF1α-puro, addgene, 114444) by a T4 ligase, and accuracy of a resulting plasmid was determined through plasmid sequencing. The lentiviral plasmid was co-transfected with viral packaging plasmids (the target plasmid, PMD2G, and PSPAX2 were in a ratio of 3:2:3) into 293 FT cells, a medium was changed at 8 h after the transfection, and a viral supernatant was collected at 72 h. A concentrate (Takara, 631231) was added to the viral supernatant, where the ratio of the viral supernatant to the concentrate was 3:1, and the resulting mixed solution was concentrated overnight at 4° C. A resulting concentrate was centrifuged at 3,000 rpm and 4° C. for 30 min, and a resulting supernatant was discarded to obtain lentiviral particles; and finally, a titer was detected, and the lentiviral particles were stored in an ultra-low temperature freezer at −80° C. The efficiency of transfection of the AQP3-CAR into T cells was shown in FIG. 2.

III. Isolation, cultivation, and lentiviral transfection of T cells:
(1) Peripheral venous blood was collected from a healthy adult and diluted with phosphate buffered saline (PBS) at 1:1, and then 15 mL of Ficoll (Cytiva, 17544652) was added per 35 mL of the peripheral blood; and a resulting mixture was subjected to Ficoll density gradient centrifugation, and a resulting intermediate white film layer was collected to obtain PBMCs.
(2) The isolated PBMCs were washed twice with PBS, then counted, then incubated at 4° C. for 30 min with CD3-positive (Miltenyi, 130-097-043) magnetic beads ($10^8$ of cells/100 µL of magnetic beads), washed twice with PBS, and allowed to pass through a column to isolate T cells. CD3/CD28 magnetic beads (a ratio of the magnetic beads to the T cells was 1:1) were added to the T cells for activation, an IL2 (proteintech, HZ-1015)-containing RPMI-1640 medium was added, and the T cells were cultivated for expansion.
(3) Resulting T cells were added to a 24-well plate, 500 µL of a medium was added, and the T cells were infected with the virus for 24 h according to a multiplicity of infection (MOI) of 20; then the medium was changed with a fresh medium, the T cells were further cultivated for 48 h, and the expression efficiency of CAR was detected by Protein-L; and when the expression efficiency of CAR was higher than 50%, AQP3-CAR-T cells were finally obtained.
(4) AQP3-CAR-T cells were further cultivated for about one week to allow in vivo and in vitro experiments.

Example 2 A Killing Experiment of the AQP3-CAR-T Cell on a Lung Cancer Cell Line H460

AQP3 is highly expressed in a variety of tumor cell lines, and is highly expressed in NSCLC cell lines H460 and A549. In the present application, the NSCLC cell line H460 with a higher AQP3 expression level was used as a target cell for in vivo and in vitro experiments.

According to ratios of 1:3 and 5:1, the AQP3-CAR-T cell and the H460 cell were mixed and added to a 24-well plate (a number of the NSCLC cell line H460 was $3\times10^4$), and normal T cells were set as a control by the same method as above; and the cells were co-cultivated for 24 h, and then a resulting supernatant was collected and detected by the ELISA method to determine an IFN-γ content. Then the T cells were washed off with PBS, the remaining tumor cells were further cultivated for one week, then fixed with 4% paraformaldehyde (PFA), stained with crystal violet, and photographed, and an area was counted.

Figure 3:
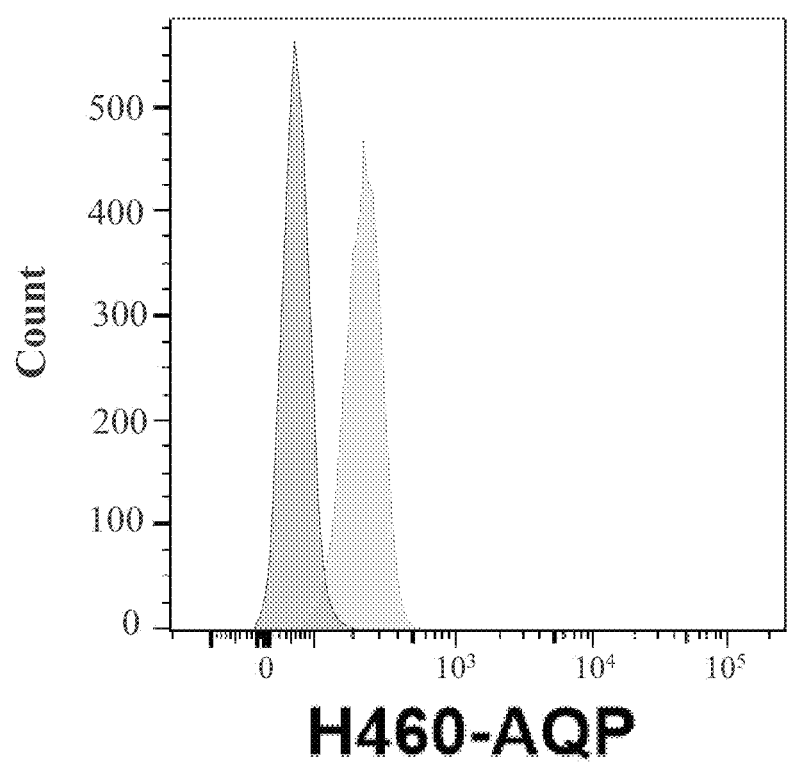
FIG. 3 shows test results of an expression level of AQP3 in an NSCLC cell line H460.

It can be seen from FIG. 3 that H460 cells die significantly under an action of AQP3-CAR-T (at a ratio of 5:1), while Normal T cells have no obvious killing effect for H460 cells at the same ratio, indicating that AQP3-CAR-T has a function of specifically killing H460.

Figure 4:
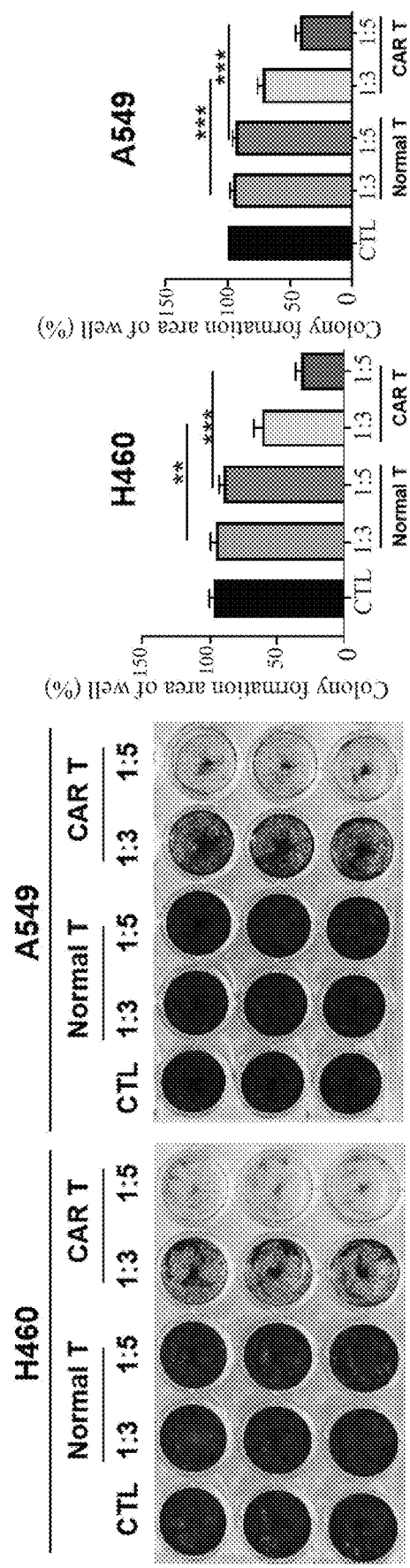
FIG. 4 shows the results of detecting the effect of CAR-T and Normal T on killing tumor cells when the ratios of target cells to effector cells are 1:3 and 1:5.

In addition, it can be seen from FIG. 4 that, after an action of AQP3-CAR-T, IFN-γ in the supernatant is increased significantly. The target cell/effector cell ratio of 1:5 is also in line with an actual situation of the use.

Figure 5:
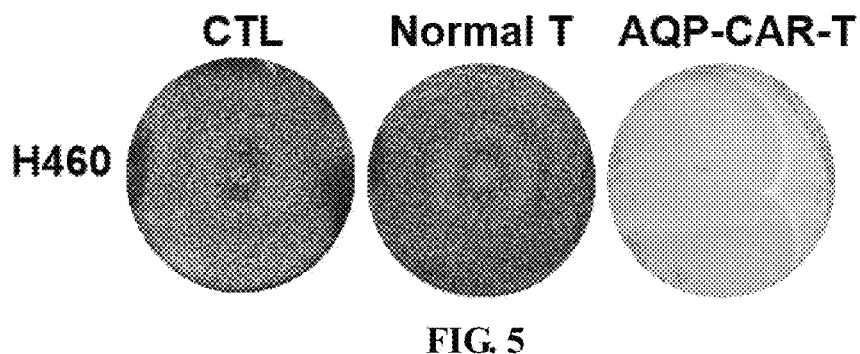
FIG. 5 shows plate images of colony formation of tumor cells after AQP3 CAR-T+H460 (5:1), Normal T+H460 (5:1), and H460 cells each are co-cultivated for 24 h, then T cells are removed, and remaining cells are further cultivated for one week.

FIG. 5 shows plate images of colony formation of tumor cells after AQP3 CAR-T+H460 (5:1), Normal T+H460 (5:1), and H460 cells each are co-cultivated for 24 h, then T cells are removed, and remaining cells are further cultivated for one week.

Example 3 A Killing Experiment of the AQP3-CAR-T Cell on a Subcutaneously Transplanted Tumor of a Lung Cancer Cell Line H460

After an in vitro killing effect was evaluated in Example 2, an in vivo killing effect was investigated.

$2\times10^6$ of H460 cells were transplanted subcutaneously into immunodeficient NSG mice. When a volume of a subcutaneous tumor reached 100 mm$^3$, the mice were randomly divided into two groups with 6 mice in each group, including an AQP-CAR-T group and a Normal T group. The mice were injected with $10^7$ of AQP3 CAR-T or Normal T cells through a tail vein, and a volume change of each mouse was recorded every two days. On day 10 after the injection, the mice were anaesthetized and sacrificed, subcutaneous tumors were collected, photographed, weighed, fixed, sectioned, and stained, and major organs of the mice were collected and fixed with formalin for later use.

Figure 6:
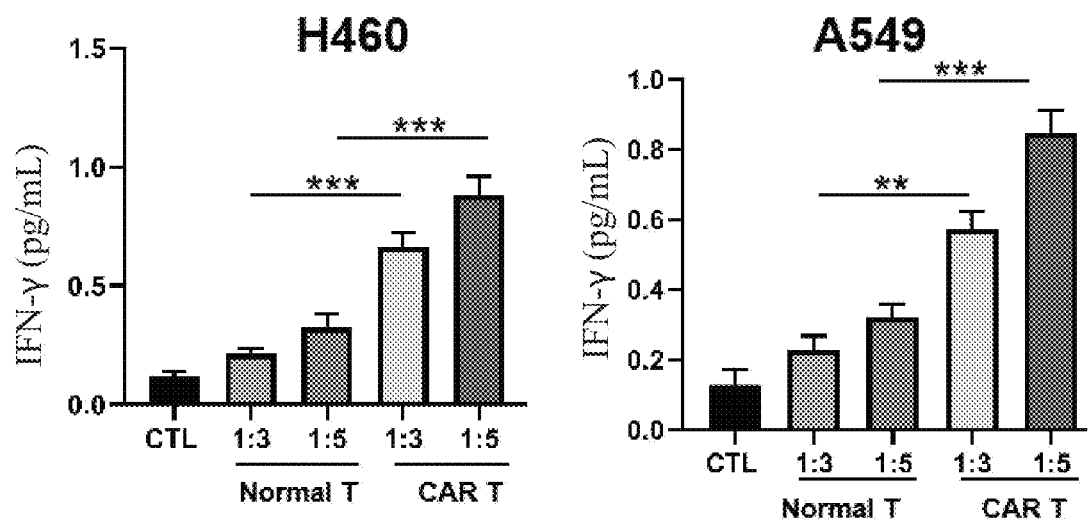
FIG. 6 shows the comparison of IFN-γ secretions of AQP3 CAR-T+H460/A549, Normal T+H460/A549, Normal T cells, and H460/A549 when the ratios of target cells to effector cells are 1:3 and 1:5, where the IFN-γ secretions are detected by the enzyme linked immunosorbent assay (ELISA) method.

FIG. 6 shows the comparison of IFN-γ secretions of AQP3-CAR-T+H460/A549, Normal T+H460/A549, Normal T cells, and H460/A549 when the ratios of target cells to effector cells are 1:3 and 1:5, where the IFN-γ secretions are detected by the ELISA method. Results: Compared with the Normal T group, the growth of subcutaneously transplanted tumors is slowed down and tumor weights are decreased in the AQP3-CAR-T treatment group. It can be known from results of tumor tissue sectioning and H&E staining that, after the AQP3-CAR-T treatment, a tumor tissue undergoes large-area necrosis and inflammatory infiltration, which fully demonstrates a potential of AQP3-CAR-T cells in the treatment of lung cancer in vivo.

Figure 7:
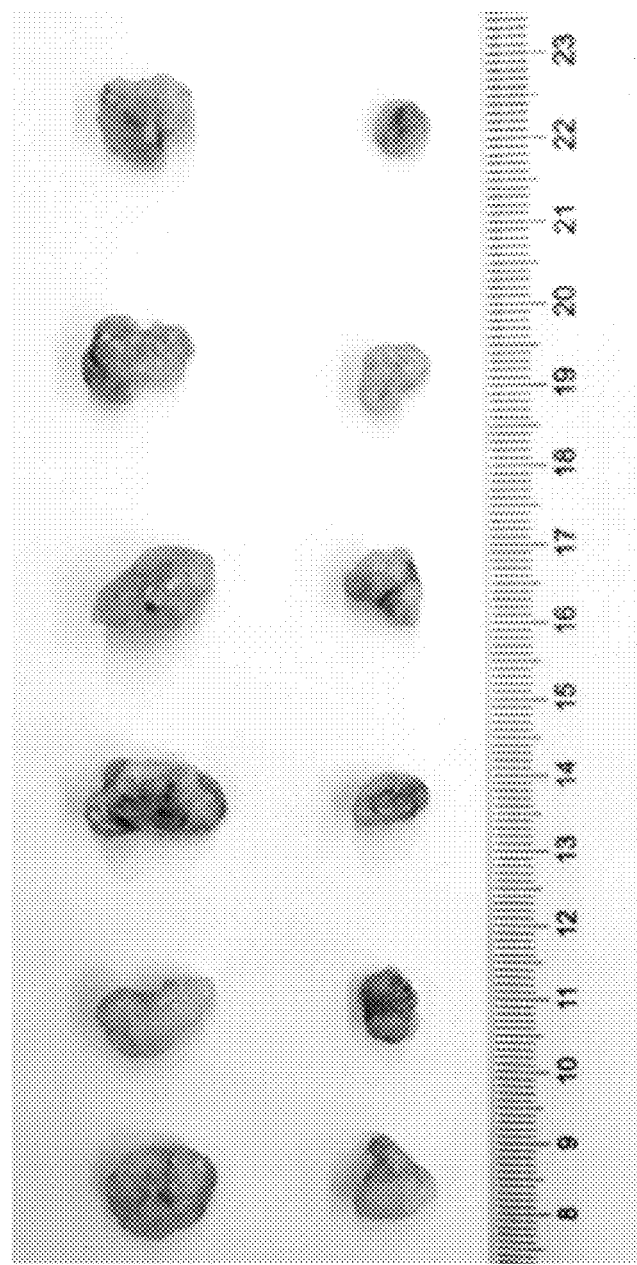
FIG. 7 shows tumors collected after subcutaneous tumorigenesis in NSG mice and then 10 days of a treatment through tail vein injection of $1\times10^7$ of APQ3-CAR-T/Normal T cells, and recorded tumor growth curves and tumor weights.
Figure 7:
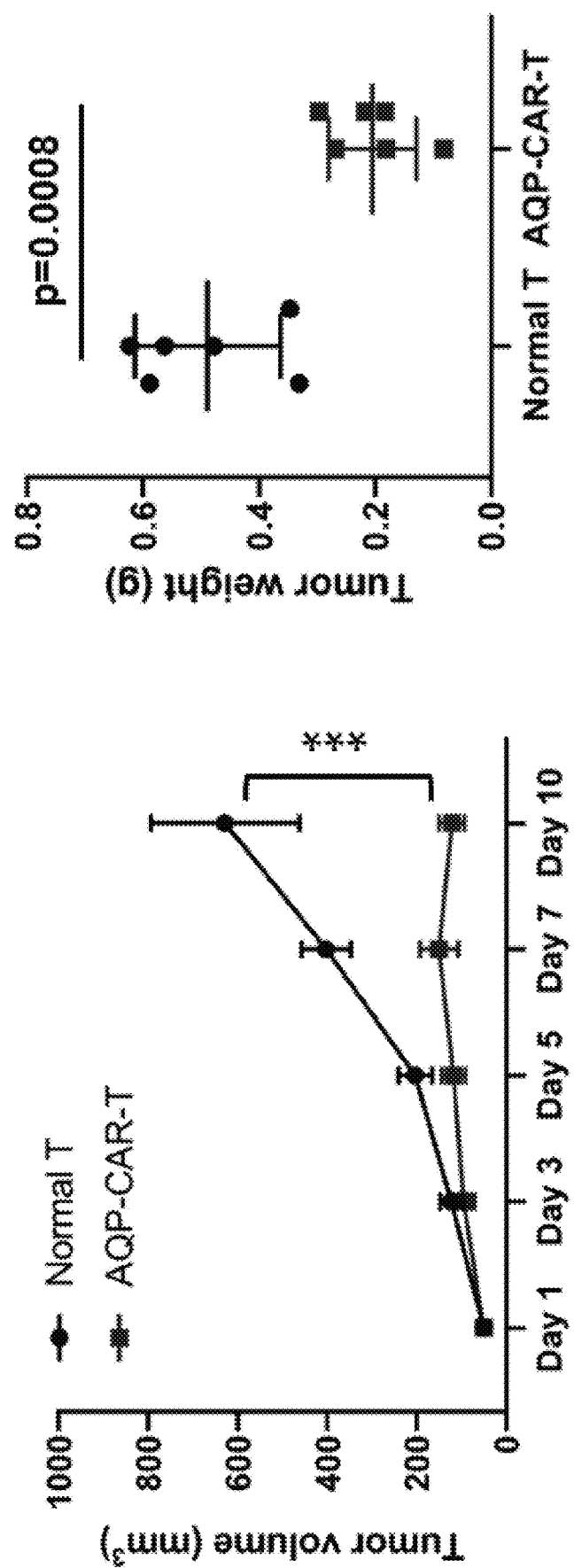
Figure 8:
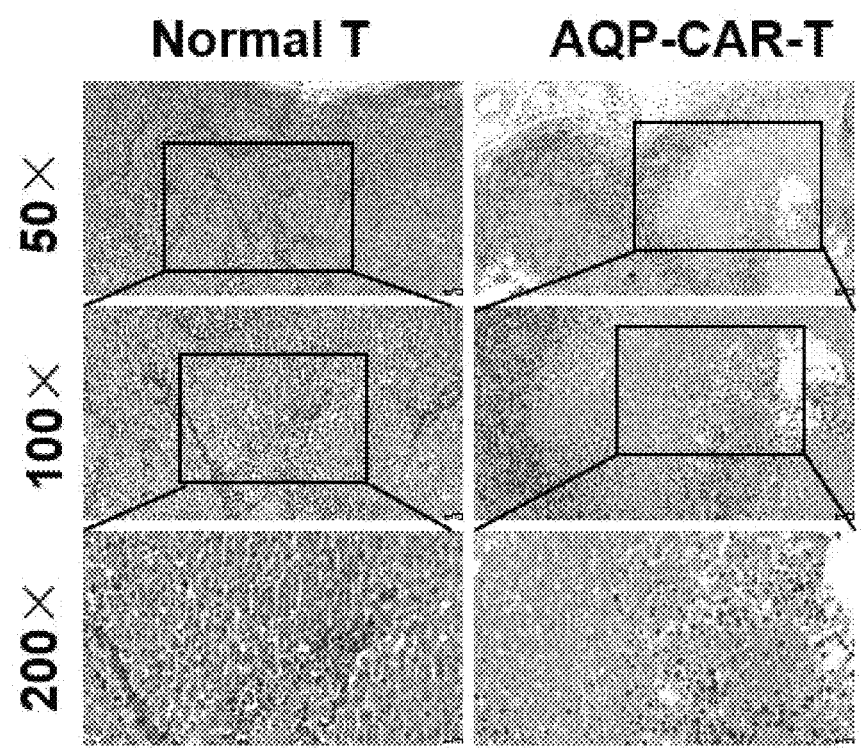
FIG. 8 shows images illustrating pathological changes of tumors collected in Example 3 that are observed after fixation, sectioning, and H&E staining of the tumors, where a lower image is an enlarged view of a rectangular zone in a corresponding upper image.

FIG. 7 shows tumors collected after subcutaneous tumorigenesis in NSG mice and then 10 days of a treatment through tail vein injection of $1\times10^7$ of APQ3-CAR-T/Normal T cells, and recorded tumor growth curves and tumor weights. After a tumor was fixed, sectioned, and subjected to H&E staining, a pathological change of a tumor was observed, as shown in FIG. 8.

Example 4 Safety Testing

Safety is an issue that must be paid attention to during CAR-T therapy, and only safe and effective CAR-T cells can be used in subsequent treatment and research. The safety of the AQP3-CAR-T cell in mice was preliminarily investigated in the present application. The major tissues and organs collected in Example 3 each were fixed, sectioned, and subjected to H&E staining, and then effects of the AQP3-CAR-T cell were determined through pathological observation; and results were shown in FIG. 9.

Figure 9:
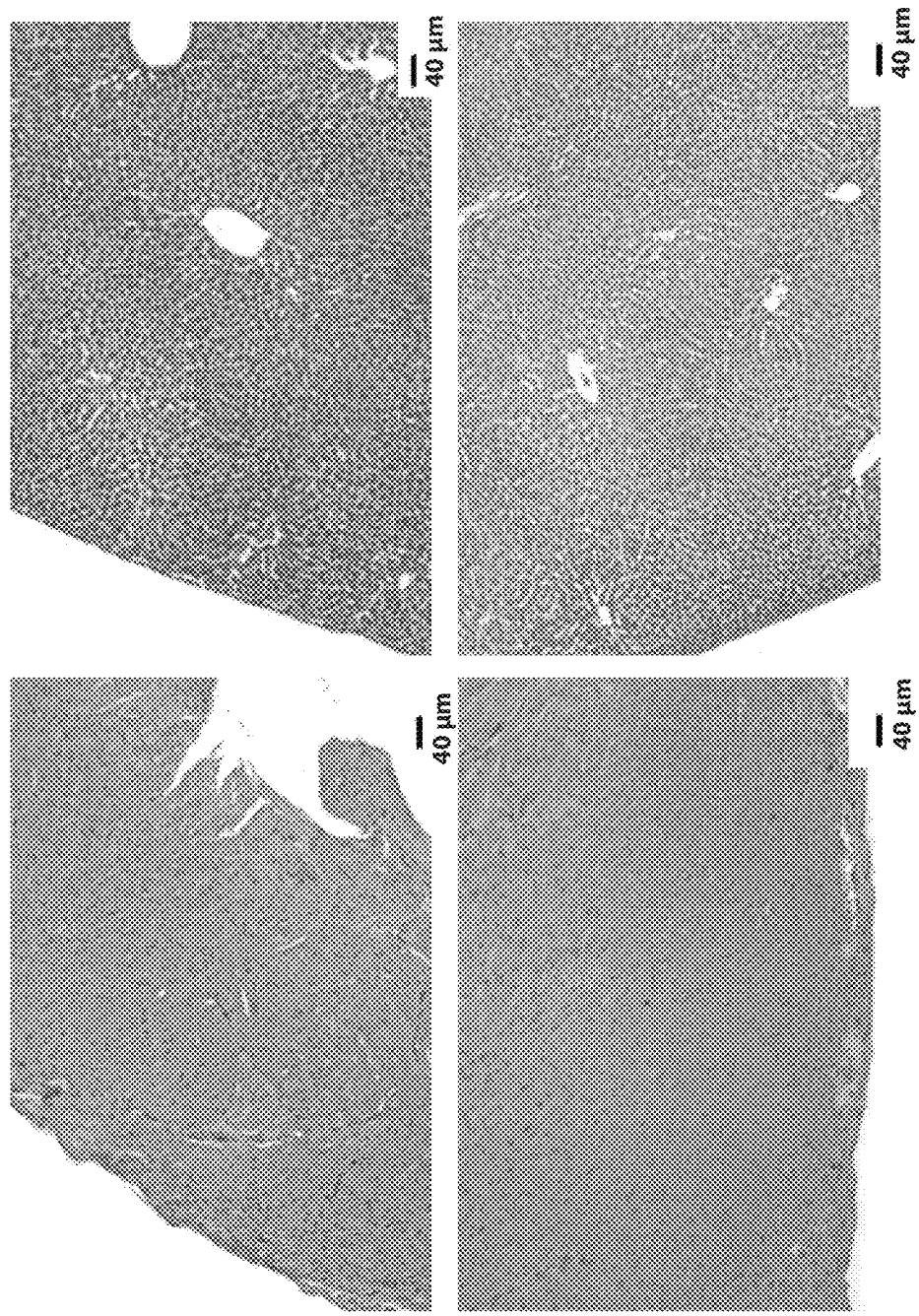
FIG. 9 shows H&E staining results of sections of major organs of mice collected on day 10 after the AQP3-CAR-T cells are injected, where pathological changes can be observed to evaluate the toxicity of the CAR-T cell on the major organs of mice.
Figure 9:
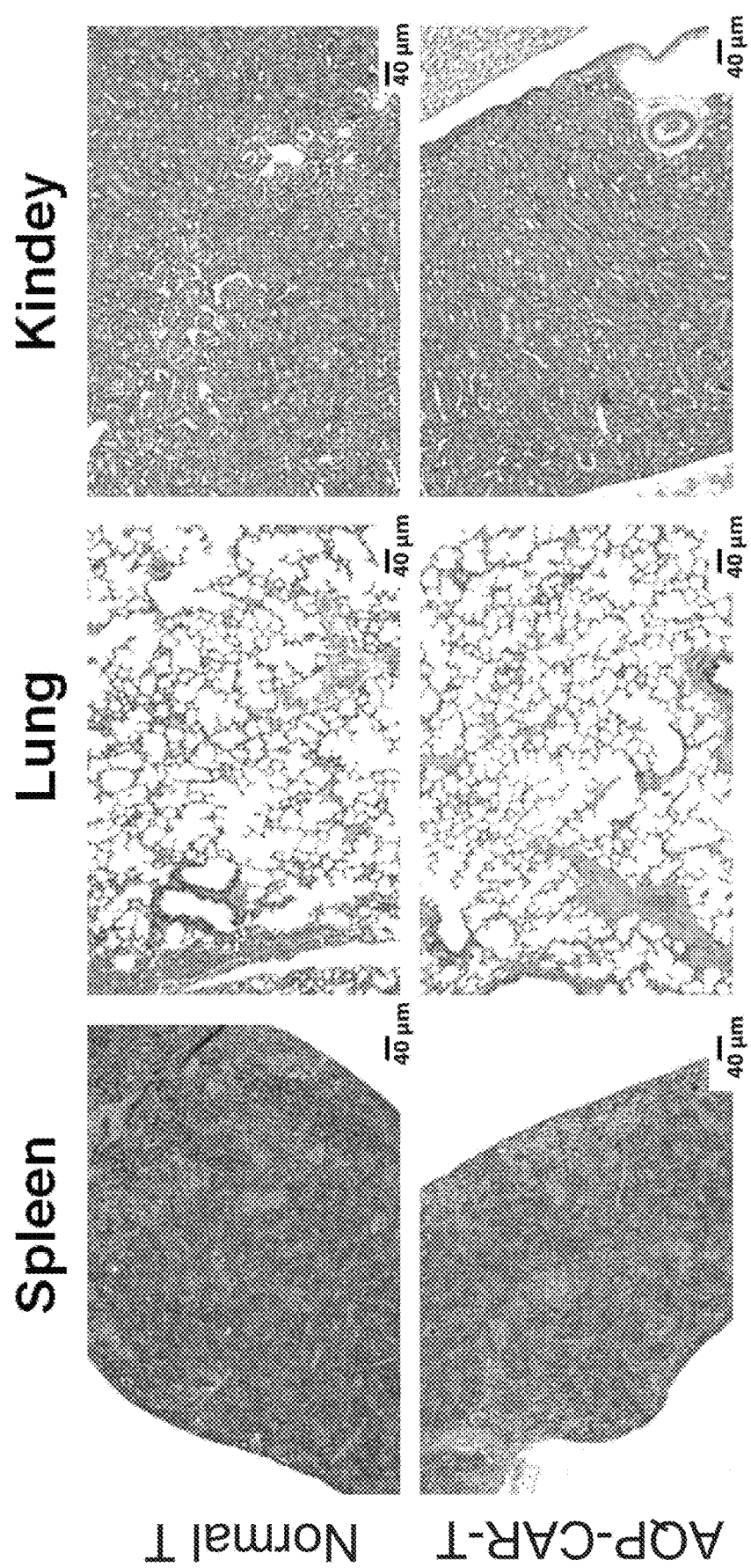

As shown in FIG. 9, compared with Normal T, the AQP3-CAR-T cell causes no obvious damage to tissues and organs (heart, liver, spleen, lung, and kidney) and also causes no obvious immune cell infiltration; and there is no obvious change in a structure of each tissue and organ. Therefore, the prepared AQP3 CAR-T cell can be preliminarily determined to be safe.

In summary, in the present application, AQP3 is innovatively adopted as a novel anti-cancer target, and AQP3 is highly expressed in both tumor cells and tumor stromal cells and can mediate the transport of both water and glycerol, which is conducive to breakage of a physical barrier of a tumor and promotes CAR-T cells to well infiltrate into a tumor to kill the tumor. The CAR fusion protein prepared by the present application can be used in the treatment of AQP3-positive malignant tumors, and especially, when used in the treatment of NSCLC, the CAR fusion protein exhibits a significant therapeutic effect. In addition, when used in the treatment of lung cancer, the CAR fusion protein causes little damage to a normal tissue and exhibits high safety. In lung cancer, AQP3 is highly expressed on a surface of tumor cells. The selection of AQP3 as a target for CAR-T therapy makes up for the lack of an effective specific target for CAR-T therapy of NSCLC and the difficulty of CAR-T to overcome a barrier of tumor stromal cells, and can also inhibit the promotion of AQP3 on the progression of a tumor, which is a therapeutic direction with many advantages.

In the description of this specification, the description with reference to the terms such as "one embodiment", "some embodiments", "an example", "a specific example", or "some examples" means that the specific features, structures, materials, or characteristics described with reference to the embodiment or example are included in at least one embodiment or example of the present application. In this specification, the schematic expression of the above terms is not necessarily directed to the same embodiment or example. Moreover, the specific features, structures, materials, or characteristics described may be combined in a suitable manner in any one or more embodiments or examples. In addition, those skilled in the art may combine different embodiments or examples described in this specification and characteristics of the different embodiments or examples without any contradiction.

Finally, it should be noted that the above examples are provided merely to describe the technical solutions of the present application, rather than to limit the protection scope of the present application. Although the present application is described in detail with reference to preferred examples, a person of ordinary skill in the art should understand that modifications or equivalent replacements may be made to the technical solutions of the present application without departing from the spirit and scope of the technical solutions of the present application.

The invention claimed is:

1. A chimeric antigen receptor T (CAR-T) cell comprising a heterologous nucleic acid encoding a CAR fusion protein, wherein the CAR fusion protein has the amino acid sequence of SEQ ID NO: 4 and targets specifically to AQP3 molecule, and wherein the CAR-T cell expresses the CAR fusion protein.

2. A drug or a preparation for treating an AQP3-positive tumor, comprising the CAR-T cell according to claim 1.

* * * * *

SEQUENCE LISTING

```
Sequence total quantity: 4
SEQ ID NO: 1           moltype = DNA  length = 690
FEATURE                Location/Qualifiers
source                 1..690
                       mol_type = other DNA
                       organism = synthetic construct
SEQUENCE: 1
gaggtgaagc tggtggagag cggcggcgac ctggtgaagc ccggcggcag cctgaagatc    60
agctgcgccg ccagcggctt caccttcagc agctacggca tgagctgggt gaggcagacc   120
cccgacaaga ggctggagtg ggtggccacc atcagcagga ggagcaccta cacctactac   180
cccgacgcg tgcagggcag gttcaccatc agcaggaca acgccaagaa caccctgtac     240
ctgcagatga gcagcctgaa gagcgaggac accgccatgt actactgcgc caggctgagc   300
ctgtacgact acgacggcgc caggtacacc atggactact ggggccaggg caccagcgtg   360
accgtgagca gcgacatcaa gatgacccag agccccaagt tcatgagcac cagcgtgggc   420
gacagggtga gcatcacctg caaggccagc caggacgtgg gcaccgccgt ggcctggtac   480
cagcagaagc ccggccagag ccccaagctg ctgatctact gggccagcac caggcacacc   540
ggcgtgcccg acaggttcac cggcagcggc agcggcaccg acttcaccct gaccatcagc   600
aacgtgcaga gcgaggacct ggccgactac ttctgccagc agtacagcag ctaccacacc   660
ttcggcgccg gcaccaagct ggagatcaag                                    690

SEQ ID NO: 2           moltype = DNA  length = 1000
FEATURE                Location/Qualifiers
source                 1..1000
                       mol_type = other DNA
                       organism = synthetic construct
SEQUENCE: 2
gctggctagg taagcttgat gctagccacc atggccttac cagtgaccgc cttgctcctg    60
ccgctggcct tgctgctcca cgccgccagg ccggaggtga agctggtgga gagcggcggc   120
gacctggtga agcccggcgg cagcctgaag atcagctgcg ccgccagcgg cttcaccttc   180
agcagctacg gcatgagctg ggtgaggcag acccccgaca gaggctgga gtgggtggcc    240
accatcagca ggaggagcac ctacacctac taccccgaca gcgtgcaggg caggttcacc   300
atcagcaggg acaacgccaa gaaccctg tacctgcaga tgagcagcct gaagagcgag    360
gacaccgcca tgtactactg cgccaggctg agcctgtacg actacgacgg cgccaggtac   420
accatggact actggggcca gggcaccagc gtgaccgtga gcagcggtgg tggtggttct   480
ggcggcggcg gctccggtgg tggtggttct ggcggcggcg gctccgacat caagatgacc   540
cagagcccca agttcatgag caccagcgtg ggcgacaggg tgagcatcac ctgcaaggcc   600
agccaggacg tgggcaccgc cgtggcctgg taccagcaga agcccggcca gagccccaag   660
ctgctgatct actgggccag caccaggcac accggcgtgc ccgacaggtt caccggcagc   720
ggcagcggca ccgacttcac cctgaccatc agcaacgtgc agagcgagga cctggccgac   780
tacttctgcc agcagtacag cagctaccac accttcggcg ccggcaccaa gctggagatc   840
aagaccacga cgccagcgcc gcgaccacca caccggcgc ccaccatcgc gtcgcagccc    900
ctgtccctgc gcccagaggc gtgccggcca cggcgggg gcgcagtgca cacgaggggg     960
ctggacttcg cctgtgatat ctacatctgg gcgcccttgg                        1000

SEQ ID NO: 3           moltype = AA  length = 230
FEATURE                Location/Qualifiers
source                 1..230
                       mol_type = protein
                       organism = synthetic construct
SEQUENCE: 3
EVKLVESGGD LVKPGGSLKI SCAASGFTFS SYGMSWVRQT PDKRLEWVAT ISRRSTYTYY    60
PDSVQGRFTI SRDNAKNTLY LQMSSLKSED TAMYYCARLS LYDYDGARYT MDYWGQGTSV   120
TVSSDIKMTQ SPKFMSTSVG DRVSITCKAS QDVGTAVAWY QQKPGQSPKL LIYWASTRHT   180
GVPDRFTGSG SGTDFTLTIS NVQSEDLADY FCQQYSSYHT FGAGTKLEIK              230

SEQ ID NO: 4           moltype = AA  length = 332
FEATURE                Location/Qualifiers
source                 1..332
                       mol_type = protein
                       organism = synthetic construct
SEQUENCE: 4
AGVSLMLATM ALPVTALLLP LALLLHAARP EVKLVESGGD LVKPGGSLKI SCAASGFTFS    60
SYGMSWVRQT PDKRLEWVAT ISRRSTYTYY PDSVQGRFTI SRDNAKNTLY LQMSSLKSED   120
TAMYYCARLS LYDYDGARYT MDYWGQGTSV TVSSGGGGSG GGGSGGGGSG GGGSDIKMTQ   180
SPKFMSTSVG DRVSITCKAS QDVGTAVAWY QQKPGQSPKL LIYWASTRHT GVPDRFTGSG   240
SGTDFTLTIS NVQSEDLADY FCQQYSSYHT FGAGTKLEIK TTTPAPRPPT PAPTIASQPL   300
SLRPEACRPA AGGAVHTRGL DFACDIYIWA PL                                 332
```